United States Patent
Dickman et al.

(10) Patent No.: US 9,744,135 B2
(45) Date of Patent: Aug. 29, 2017

(54) FAST DISINTEGRATING COMPOSITIONS AND TABLETS THEREOF

(71) Applicants: Robert F. Dickman, St. George, UT (US); Scott Gubler, St. George, UT (US); Tim Olds, Washington, UT (US); R. Vance Wood, Hurricane, UT (US); Usha Tuscano, St. George, UT (US); Angel Gonzalez, Ivins, UT (US)

(72) Inventors: Robert F. Dickman, St. George, UT (US); Scott Gubler, St. George, UT (US); Tim Olds, Washington, UT (US); R. Vance Wood, Hurricane, UT (US); Usha Tuscano, St. George, UT (US); Angel Gonzalez, Ivins, UT (US)

(73) Assignee: Deseret Laboratories, Inc., St. George, UT (US)

( * ) Notice: Subject to any disclaimer, the term of this patent is extended or adjusted under 35 U.S.C. 154(b) by 0 days.

(21) Appl. No.: 15/054,999

(22) Filed: Feb. 26, 2016

(65) Prior Publication Data
US 2016/0250335 A1   Sep. 1, 2016

Related U.S. Application Data

(60) Provisional application No. 62/126,275, filed on Feb. 27, 2015.

(51) Int. Cl.
*A61K 47/32* (2006.01)
*A61K 9/20* (2006.01)
*A61K 9/00* (2006.01)

(52) U.S. Cl.
CPC .......... *A61K 9/2027* (2013.01); *A61K 9/0056* (2013.01); *A61K 9/2018* (2013.01)

(58) Field of Classification Search
CPC ... A61K 9/2027; A61K 9/2018; A61K 9/0056
USPC ...................................... 514/772.5
See application file for complete search history.

(56) References Cited

U.S. PATENT DOCUMENTS

| | | |
|---|---|---|
| 5,958,453 A | 9/1999 | Ohno et al. |
| 6,248,357 B1 | 6/2001 | Ohno et al. |
| 7,070,805 B2 | 7/2006 | Shimizu et al. |
| 7,399,485 B1 | 7/2008 | Shimizu et al. |
| 7,560,576 B2 | 7/2009 | Dancer et al. |
| 7,834,201 B2 | 11/2010 | Dancer et al. |
| 7,875,292 B2 | 1/2011 | Shimizu et al. |
| 2006/0057207 A1* | 3/2006 | Ziegler ............ A61K 9/0056 424/484 |
| 2010/0178353 A1 | 7/2010 | Mezaache et al. |

FOREIGN PATENT DOCUMENTS

| | | |
|---|---|---|
| EP | 0371466 A1 | 11/1989 |
| EP | 0839526 A2 | 10/1997 |

* cited by examiner

*Primary Examiner* — Yevegeny Valenrod
(74) *Attorney, Agent, or Firm* — Brinks Gilson & Lione; Ryan L. Marshall; Jonathan Hartley

(57) ABSTRACT

Compositions useful for making dosage forms capable of dissolving or disintegrating in less than 10 seconds without the need for conventional disintegrants and methods making and using the same are disclosed.

18 Claims, No Drawings

FAST DISINTEGRATING COMPOSITIONS AND TABLETS THEREOF

REFERNCE TO EARLIER FILED APPLICATIONS

This application claims the benefit under 35 U.S.C. §119(e) of U.S. Provisional Application No. 62/126,275, filed Feb. 27, 2015, the disclosure of which is incorporated, in their entirety, by this reference.

TECHNICAL FIELD OF THE INVENTION

The invention relates to compositions and dosage forms based thereon, such as tablets and lozenges, when taken orally, quickly dissolves in the mouth and gastrointestinal track.

BACKGROUND

There has been widespread use of tablets since the latter part of the 19th century, and the majority of pharmaceutical dosage forms are marketed as tablets. Tablet popularity as a dosage form among pharmaceutical manufacturers arises from its simplicity, low cost, and the speed of production. Other reasons include stability of drug product, convenience in packaging, shipping, and dispensing. To the patient or consumer, tablets offer convenience of administration, ease of accurate dosage, compactness, portability, blandness of taste, ease of administration, and elegant distinctive appearance.

Fast dissolving and disintegrating tablets (FDTs) have received ever-increasing demand during the last decade, and the field has become a rapidly growing area in the pharmaceutical and supplement industries. Oral drug delivery remains the preferred route for administration of various drugs. Recent developments in the technology have prompted scientists to develop FDTs that improve patient compliance, bioavailability, and convenience. Upon introduction into the mouth, these tablets dissolve or disintegrate mostly in the mouth for easy administration of active pharmaceutical ingredients. FDTs are solid unit dosage forms, which disintegrate or dissolve rapidly in the. FDTs provide an advantage particularly for pediatric and geriatric populations who have difficulty in swallowing conventional tablets and capsules. Notwithstanding this increased attention, there remains a need to provide alternative formulations for formulating FDTs for improved buccal, sublingual, and gastrointestinal absorption and release.

SUMMARY

In one aspect, a rapidly dissolving dosage form is disclosed which includes (a) a sugar alcohol; (b) polyvinylpolypyrrolidone; (c) sodium stearyl fumarate; and (d) an active ingredient.

In one aspect, a rapidly dissolving dosage form is disclosed which consists only of (a) a sugar alcohol; (b) polyvinylpolypyrrolidone; (c) sodium stearyl fumarate; and (d) an active ingredient.

In some embodiments, the sugar alcohol is mannitol.

In some embodiments, the sugar alcohol is present at a concentration of between about 20% to about 80% by weight, the polyvinylpolypyrrolidone is present at a concentration of about 9% to about 60% by weight, the sodium stearyl fumarate is present at a concentration of about 1% to about 30% by weight, and the active ingredient is present at about 10% or less by weight.

In some embodiments, the dosage dissolves in less than about 10 seconds. In some embodiments, the dissolution is sublingual. In some embodiments, the dissolution is buccal. In some embodiments, the dissolution is oral. In some embodiments, the dissolution is esophageal. In some embodiments, the dosage dissolves in less than about 5 seconds.

In another aspect, a method of administering an active ingredient to a patient, includes providing the dosage form as described herein to a patient in need thereof.

In another aspect, a method of preparing a dosage form, includes providing a sugar alcohol, polyvinylpolypyrrolidone, sodium stearyl fumarate, and an active ingredient; and compressing the sugar alcohol, polyvinylpolypyrrolidone, sodium stearyl fumarate, and active ingredient. In some embodiments, the sugar alcohol is mannitol.

DETAILED DESCRIPTION

While the terminology used in this application is standard within the art, the following definitions of certain terms are provided to assure clarity.

Units, prefixes, and symbols may be denoted in their SI accepted form. Numeric ranges recited herein are inclusive of the numbers defining the range and include and are supportive of each integer within the defined range. Unless otherwise noted, the terms "a" or "an" are to be construed as meaning "at least one of." The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

The term "tablet" includes solid dosage pharmaceutical and supplement forms containing drug substances with or without suitable fillers. They are produced by compression or compaction of a formulation containing the drug, active ingredient, and excipients selected to aid in the processing and to improve the properties of the product. Tablets may be coated or uncoated. They may include various diluents, binders, disintegrants, lubricants, glidants and in many cases, colorants. Excipients used are classified according to the function they perform. For example, a glidant may be used to improve the flow of powder blend in the hopper and into the tablet die.

The terms "treatment," "treating," and "treat," as used herein, include their generally accepted meanings, i.e., the management and care of a patient for the purpose of preventing, reducing the risk in incurring or developing a given condition or disease, prohibiting, restraining, alleviating, ameliorating, slowing, stopping, delaying, or reversing the progression or severity, and holding in check and/or treating existing characteristics, of a disease, disorder, or pathological condition, described herein, including the alleviation or relief of symptoms or complications, or the cure or elimination of the disease, disorder, or condition. The present methods include both medical, therapeutic, and/or prophylactic treatment, as appropriate.

The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

Fast disintegrating tablets (FDTs) are meant for administration to any who can ingest oral or suppository medications and supplements and particularly to patients who cannot swallow, such as the elderly, stroke victims, bedridden patients, patients affected by renal failure, and patients who refuse to swallow, such as pediatric, geriatric, and psychiatric patients. By the use of FDTs, rapid drug or other active ingredient therapy intervention can be achieved, achieve increased bioavailability/rapid absorption through pregastric absorption of drugs or other active ingredients from mouth, pharynx, and esophagus as saliva passes down. FDTs are convenient for administration and patient compliant for disabled, bedridden patients, and for travelers and busy people who do not always have access to water. Their good mouth feel property helps to change the perception of medication as bitter pill, particularly in pediatric patients. The risk of chocking or suffocation during oral administration of conventional formulations due to physical obstruction is diminished, thus providing improved safety and efficacy of the active. In addition, some drug products or active ingredients cannot be effectively delivered in the environment of the gastrointestinal tract, so sublingual or buccal delivery may be the only bioavailable delivery available. The new business opportunity like product differentiation, product promotion, patent extension, and life cycle management become easy after the intervention of FDTs.

Recently, the European Pharmacopoeia adopted the term orodispersible tablet as a tablet to be placed in the mouth where it disperses rapidly before swallowing and which disintegrates in less than 3 minutes. There was no specification concerning either the hardness or the friability of this kind of tablets. That is why we find certain Rapidly Disintegrating Tablets (RDT) in the market that disintegrate in less than 1 minute or maybe 30 seconds, but are brittle and require specified peelable blister packaging and thus higher costs.

Tablets may be plain, film or sugar coated, bisected, embossed, layered, or sustained release. They can be made in a variety of sizes, shapes and colors. Tablets may be swallowed, chewed, or dissolved in the buccal cavity or beneath the tongue (sublingual), or delivered esophageal or gastrointestinal. They may be dissolved in water for local or topical application. Sterile tablets are normally used for parenteral solutions.

In addition to the active or therapeutic ingredients, tablets may contain a number of inert materials known as excipients. They may be classified according to the role they play in the final tablet. The primary composition includes a filler, binder, lubricant, and glidant. Other excipients which give physical characteristics to the finished tablet are coloring agents, and flavors in the case of chewable tablets. Without excipients most drugs and active ingredients cannot be directly compressed into tablets. This is primarily due to the poor flow and cohesive properties of most drugs and active ingredients. Typically, excipients are added to a formulation to impart good flow and compression characteristics to the material being compressed. Such properties are imparted to these excipients through pretreatment steps such as wet granulation, slugging, spray drying spheronization, or crystallization.

Lubricants are typically added to prevent the tableting materials from sticking to punches, minimize friction during tablet compression, and allow for removal of the compressed tablet from the die. Such lubricants are commonly included in the final tablet mix in amounts usually less than 1% by weight.

In addition, tablets often contain diluents which are added to increase the bulk weight of the blend resulting in a practical size for compression. This is often necessary where the dose of the drug or active ingredient is relatively small.

Another commonly used class of excipients in tablets is binders. Binders are agents, which impart cohesive qualities to the powdered material. Commonly used binders include starch, and sugars such as sucrose, glucose, dextrose, and lactose.

Disintegrants are often included to ensure that the tablet has an acceptable rate of disintegration. Typical disintegrants include starch derivatives and salts of carboxymethylcellulose.

Other desirable characteristics of excipients include the following: (1) high compressibility to allow strong tablets to be made at low compression forces; (2) good flow properties that can improve the flow of other excipients in the formula; and (3) cohesiveness (to prevent tablet from crumbling during processing, shipping and handling).

Some of the processes for making compressed tablets are wet granulation, direct compression, and dry granulation (slugging or roller compaction). The method of preparation and type of excipients are selected to give the tablet formulation the desired physical characteristics that allow for the rapid compression and later dissolution or disintegration of the tablets. After compression, the tablets must have a number of additional attributes such as appearance, hardness, disintegrating ability, and an acceptable dissolution profile. Choice of fillers and other excipients will depend on the chemical and physical properties of the drug or other active ingredient, behavior of the mixture during processing, and the properties of the final tablets. Preformulation studies are done to determine the chemical and physical compatibility of the active component with proposed excipients.

The properties of the drug or its active ingredient, its dosage forms, and the economics of the operation will determine selection of the best process for tableting. Generally, both wet granulation and direct compression can be used in developing a tablet.

The dry granulation method may be used where one of the constituents, either the drug or active ingredient or the diluent, has sufficient cohesive properties to be tableted. The method consists of blending, slugging, and roller compaction for the the ingredients, dry screening, lubrication, and compression.

The wet granulation method is used to convert a powder mixture into granules having suitable flow and cohesive properties for tableting for high sheer or fluid bed techniques. The procedure consists of mixing the powders in a suitable blender followed by adding the granulating solution under shear or in a fluid bed to the mixed powders to obtain a granulation. The overall process includes: weighing, dry powder blending, wet granulating, drying, milling, blending lubrication and compression.

In general, powders do not have sufficient adhesive or cohesive properties to form hard, strong granules. A binder is usually required to bond the powder particles together due to the poor cohesive properties of most powders. Heat and moisture sensitive drugs or active ingredients cannot usually be manufactured using wet granulation. The large number of processing steps and processing time are problems due to high level manufacturing costs. Wet granulation has also been known to reduce the compressibility of some pharmaceutical excipients such as microcrystalline cellulose.

Direct compression is regarded as a relatively quick process where the powdered materials are compressed directly without changing the physical and chemical properties of the drug or active ingredient. The active ingredient(s), direct compression excipients and other auxiliary substances, such as a glidant and lubricant are blended in a twin shell blender or similar low shear apparatus before being compressed into tablets. This type of mixing was believed to be essential in order to prepare "pharmaceutically acceptable" dosage forms. For example, Remington's Pharmaceutical Sciences (RPS), pages 1203 to 1932 17th edition (1985), cautions pharmaceutical scientists that the manner in which a lubricant is added to a formulation must be carefully controlled.

Accordingly, lubricants are usually added to a granulation by gentle mixing. RPS warns that prolonged blending of a lubricant with a granulation can materially affect hardness and disintegration time for the resulting tablets. Furthermore, Ansel et al (1995) Pharmaceutical Dosage Forms and Drug Delivery Systems, 6.sup.th Ed. p. 199, indicates that excessive blending of lubricants with the granulate ingredients cause water proofing of the granule and reduces tablet hardness or strength of the compressed tablet. For these reasons, high shear mixing conditions have not been used to prepare direct compression dosage forms.

The advantages of direct compression include uniformity of blend, few manufacturing steps involved, (i.e. the overall process involves weighing of powders, blending and compression, hence less cost), elimination of heat and moisture, prime particle dissociation, and physical stability.

Rapidly dissolving tablets or lozenges in the present disclosure include a combination of ingredients that when formulated as an excipient in a FTD tablet and combined with a drug or active ingredient can create a rapid dissolve excipient faster than conventional formulations. Such tablets can have a dissolution rate in the mouth (oral cavity) of less than about 10 seconds. In some embodiments, the rate of dissolution is less than about 5 seconds. The compositions may have low hardness but good physical stability. This would also allow for standard bottle packaging as well as specialty packaging and convenient handling.

A first ingredient in the rapidly dissolving excipient is a sugar alcohol. The sugar alcohol may be any suitable sugar alcohol for human consumption. Sugar alcohols include glycerol (3-carbon), erythritol (4-carbon), threitol (4-carbon), arabitol (5-carbon), xylitol (5-carbon), ribitol (5-carbon), mannitol (6-carbon), sorbitol (6-carbon), galactitol (6-carbon), fucitol (6-carbon), iditol (6-carbon), inositol (6-carbon; a cyclic sugar alcohol), volemitol (7-carbon), isomalt (12-carbon), maltitol (12-carbon), lactitol (12-carbon), maltotriitol (18-carbon), and maltotetraitol (24-carbon), among others. In one embodiment, the sugar alcohol is mannitol. In some embodiments, the amount of sugar alcohol present is between about 20% and about 80% by weight of the total composition.

A second ingredient in the rapidly dissolving excipient is polyvinylpolypyrrolidone. In some embodiments, the amount of polyvinylpolypyrrolidone present is between about 9% and about 60% by weight of the total composition.

A third ingredient in the rapidly dissolving excipient is sodium stearyl fumarate. In some embodiments, the amount of sodium stearyl fumarate present is between about 1% and about 30% by weight of the total composition.

A fourth ingredient in the rapidly dissolving tablet is an active ingredient. In some embodiments, the amount of active ingredient is about 10% or less by weight of the total composition. Suitable active ingredients include those approved by regulatory agencies including the U.S. Food and Drug Administration and those which are used nutritional supplements. Suitable active ingredients also include those which are homeopathic in nature.

Having thus described exemplary embodiments of the present invention, it should be noted by those of ordinary skill in the art that the within disclosures are exemplary only and that various other alternatives, adaptations, and modifications may be made within the scope of the present invention. Accordingly, the present invention is not limited to the specific embodiments illustrated herein.

EXAMPLES

A tablet was prepared using the following constituent proportions: mannitol -83.3%, polyvinylpolypyrrolidone - 9.3%, sodium stearyl fumarate - 1.9%, and the balance made up of starch and homeopathic ingredients in water and alcohol that is evaporated to dryness - 5.5%, all in weight percent of the total composition.

The invention claimed is:
1. A rapidly dissolving dosage form, consisting of:
    (a) a sugar alcohol;
    (b) polyvinylpolypyrrolidone;
    (c) sodium stearyl fumarate;
    (d) an active ingredient.
2. The dosage form of claim 1, wherein the sugar alcohol is mannitol.
3. The dosage form of claim 1, wherein the sugar alcohol is present at a concentration of between 20% to 80% by weight, the polyvinylpolypyrrolidone is present at a concentration of 9% to 60% by weight, the sodium stearyl fumarate is present at a concentration of 1% to 30% by weight, and the active ingredient is present at 10% or less by weight.
4. The dosage form of claim 1, wherein the dosage form dissolves in less than 10 seconds.
5. The dosage form of claim 1, wherein the dosage form dissolves in less than 5 seconds.
6. A method of administering an active ingredient to a patient, comprising providing the dosage form of claim 1 to a patient in need thereof.
7. A method of preparing a dosage form, comprising:
    providing a composition consisting of a sugar alcohol, polyvinylpolypyrrolidone, sodium stearyl fumarate, and an active ingredient; and
    compressing the sugar alcohol, polyvinylpolypyrrolidone, sodium stearyl fumarate, and active ingredient.
8. The method of claim 7, wherein the sugar alcohol is mannitol.
9. The dosage form of claim 2, wherein the sugar alcohol is present at a concentration of between 20% to 80% by weight, the polyvinylpolypyrrolidone is present at a concentration of 9% to 60% by weight, the sodium stearyl fumarate is present at a concentration of 1% to 30% by weight, and the active ingredient is present at 10% or less by weight.
10. The dosage form of claim 9, wherein the dosage form dissolves in less than 10 seconds.
11. The dosage form of claim 9, wherein the dosage form dissolves in less than 5 seconds.
12. A method of administering an active ingredient to a patient, comprising providing the dosage form of claim 2 to a patient in need thereof.
13. A method of administering an active ingredient to a patient, comprising providing the dosage form of claim 3 to a patient in need thereof.
14. A method of administering an active ingredient to a patient, comprising providing the dosage form of claim 4 to a patient in need thereof.

15. A method of administering an active ingredient to a patient, comprising providing the dosage form of claim 5 to a patient in need thereof.

16. A method of administering an active ingredient to a patient, comprising providing the dosage form of claim 9 to a patient in need thereof.

17. A method of administering an active ingredient to a patient, comprising providing the dosage form of claim 10 to a patient in need thereof.

18. A method of administering an active ingredient to a patient, comprising providing the dosage form of claim 11 to a patient in need thereof.

\* \* \* \* \*